US00PP11789P2

(12) United States Plant Patent
Churchus

(10) Patent No.: US PP11,789 P2
(45) Date of Patent: Feb. 27, 2001

(54) KALANCHOE PLANT NAMED 'ELVES BELLS'

(75) Inventor: John Churchus, Victoria (AU)

(73) Assignee: Outeniqua Protea Nursery, Emerald (AU)

( * ) Notice: Subject to any disclaimer, the term of this patent is extended or adjusted under 35 U.S.C. 154(b) by 0 days.

(21) Appl. No.: 09/334,020

(22) Filed: Jun. 15, 1999

(51) Int. Cl.[7] ..... A01H 5/00

(52) U.S. Cl. ..... Plt./335

(58) Field of Search ..... Plt./335, 341, 340, Plt./339, 337

*Primary Examiner*—Michelle Kizilkaya
(74) *Attorney, Agent, or Firm*—C. A. Whealy

(57) ABSTRACT

A distinct cultivar of Kalanchoe plant named 'Elves Bells', characterized by its upright and spreading and/or weeping plant habit; very freely clumping growth habit; dark green, succulent, irregularly-serrated, oblanceolate foliage; and large elongated urceolate dull purplish red flowers arranged in loose terminal cymes.

2 Drawing Sheets

BACKGROUND OF THE INVENTION

The present invention relates to a new and distinct cultivar of Kalanchoe plant, botanically known as *Kalanchoe hybrida*, and hereinafter referred to by the cultivar name Elves Bells.

The new Kalanchoe is a product of a planned breeding program conducted by the Inventor in Devon Meadows, Victoria, Australia. The objective of the breeding program was to create new bell-type Kalanchoe cultivars with clumping growth habit, large flowers and interesting flower colors.

The new Kalanchoe originated from a cross made by the Inventor of an unnamed selection of *Kalanchoe hybrida* as the male, or pollen, parent with the *Kalanchoe hybrida* cultivar Pixie Bells, not patented, as the female or seed parent. The cultivar Elves Bells was discovered and selected by the Inventor as a flowering plant within the progeny of the stated cross in a controlled environment in Devon Meadows, Victoria, Australia, in 1995.

Asexual reproduction of the new Kalanchoe by terminal cuttings taken at Devon Meadows, Victoria, Australia, has shown that the unique features of this new Kalanchoe are stable and reproduced true to type in successive generations.

BRIEF SUMMARY OF THE INVENTION

The cultivar Elves Bells has not been observed under all possible environmental conditions. The phenotype may vary somewhat with variations in enviroment such as temperature, daylength and light intensity, without, however, any variance in genotype.

The following traits have been repeatedly observed and are determined to be the unique characteristics of 'Elves Bells'. These characteristics in combination distinguish 'Elves Bells' as a new and distinct cultivar:

1. Upright to spreading and/or weeping plant habit.
2. Very freely clumping growth habit.
3. Dark green, succulent, irregularly-serrated, oblanceolate foliage.
4. Large elongated urceolate dull purplish red flowers arranged in loose terminal cymes.

The new Kalanchoe can be compared to the female parent, the cultivar Pixie Bells. Plants of the new Kalanchoe differs from plants of the cultivar Pixie Bells in the following characteristics:

1. Plants of the new Kalanchoe are more freely clumping and have stronger stems than plants of the cultivar Pixie Bells.
2. Plants of the new Kalanchoe have narrower leaves than plants of the cultivar Pixie Bells.
3. Plants of the new Kalanchoe are more floriferous than plants of the cultivar Pixie Bells.
4. Flowers of plants of the new Kalanchoe are darker purple red than flowers of plants of the cultivar Pixie Bells.

BRIEF DESCRIPTION OF THE PHOTOGRAPHS

The accompanying colored photographs illustrate the overall appearance of the new Kalanchoe, showing the colors as true as it is reasonably possible to obtain in colored reproductions of this type.

The photograph at the top of the first sheet comprises a side perspective view of a typical flowering plant of 'Elves Bells'.

The photograph at the bottom of the first sheet comprises a close-up view of a typical leaves and flowers of 'Elves Bells'.

The photograph on the second sheet is a close-up view of the base of a typical plant of 'Elves Bells' showing the freely clumping growth habit. Flower and foliage colors in the photographs may appear different from the actual colors due to light reflectance. Plants depicted in the photographs were of the same age and grown under the same environmental conditions as described in the detailed botanical description.

DETAILED BOTANICAL DESCRIPTION

The following observations, measurements and values describe three plants of the Kalanchoe grown in one-gallon containers in Bonsall, Calif., in a polyethylene-covered greenhouse with day temperatures ranging from 21 to 29° C. and night temperatures about 18° C. and light levels of about 4,000 to 5,000 foot-candles. Plants were exposed to long nyctoperiods/short photoperiods to induce flower initiation and development.

In the following description, color references are made to The Royal Horticultural Society Colour Chart except where general terms of ordinary dictionary significance are used. The plants described were about 16 and 18 weeks of age from propagation of unrooted cuttings.

Botanical classification: *Kalanchoe hybrida* cultivar Elves Bells.

Parentage:

*Male or pollen parent.*—Unnamed selection of *Kalanchoe hybrida.*

*Female or seed parent.*—*Kalanchoe hybrida* cultivar Pixie Bells (not patented).

Propagation:

*Type cutting.*—Terminal cuttings.

*Time to initiate roots, summer.*—About 7 to 10 days at 22° C.

*Time to initiate roots, winter.*—About 18 days at 15° C.

*Time to develop roots, summer.*—About 28 days at 22° C.

*Time to develop roots, winter.*—About 30 days at 15° C.

*Rooting habit.*—Numerous, fine, fibrous, and well-branched.

Plant description:

*Form.*—Upright to spreading and/or weeping; mounding. Freely clumping with numerous shoots at the base of the plant, typically about 40 shoots per plant. Succulent.

*Branching habit.*—Freely branching. Pinching (removal of terminal apex) will enhance development of lateral branches.

*Plant height at flowering.*—About 24 cm.

*Plant diameter at flowering.*—About 42 cm.

*Growth rate/vigor.*—Moderate.

*Stem description.*—Lateral branch length: About 21 cm. Lateral branch diameter: About 7 mm. Main stem diameter at soil level: About 1.5 cm. Internode length: About 9 mm. Texture: Smooth, glabrous. Stem Color: 147C with anthocyanin tinge, 59C.

*Foliage description.*—Leaves simple, opposite, generally symmetrical. Quantity of leaves per lateral branch: About 50. Length: About 5 cm. Width: About 1.75 cm. Thickness: About 3 mm. Shape: Oblanceolate. Apex: Broadly acute. Base: Acute. Margin: Irregularly serrated. Texture: Smooth, succulent; shiny; thick cuticle. Petiole length: About 2 cm. Petiole diameter: About 3 mm. Color: Young foliage, upper surface: 144A. Young foliage, lower surface: 144B. Mature foliage, upper surface: 147A; leaf apices may be reddish (anthocyanin) under high light conditions. Mature foliage, lower surface: 147B. Petiole: 147B.

Flower description:

*Flower type and habit.*—Single elongated urceolate flowers arranged in loose dichasial terminal cymes. Flowers hang from curved pedicels at about a 30° angle, nodding. Flowers persistent.

*Quantity of flowers.*—Typically about 12 per cyme.

*Natural flowering season.*—Late autumn/winter/early spring; flower initiation and development can be induced under long nyctoperiod/short photoperiod.

*Inflorescences borne.*—Above foliage, arising from leaf axils.

*Time to flower.*—About 12 weeks when exposed to inductive long nyctoperiod/short photoperiod treatments. Time to flower may also depend on temperature and light intensity.

*Flower diameter.*—Apex: About 1.4 cm. Mid-section, at widest part of corolla: About 1.2 cm. Base: About 5 mm.

*Flower length.*—About 2.9 cm.

*Flower longevity.*—Very long-lived, flowers last about 2 to 3 weeks on the plant.

*Petals.*—Quantity: Four petals fused at base to form elongated urceolate corolla with reflexed apex. Length: About 3 cm. Width, separated petals distal to fused tube: About 6 mm. Shape: Elongated elliptic. Apex: Broadly acute. Margin: Entire. Texture: Glabrous, smooth, somewhat shiny. Color: When opening, upper surface: Apex, 150A; throat, 186B. When opening, lower surface: Apex, 150A; tube, 186A. Mature, upper surface: Apex, 150B; throat, 186B tinted with 150B. Mature, lower surface: Apex, 1C; tube, 186A; tube color fades to 186B with subsequent development.

*Sepals.*—Quantity: Four sepals fused at the base to form a single whorl forming a slightly cupped to flat platform subtending the corolla. Calyx length: About 7 mm. Calyx width: About 1.1 cm. Shape: Broadly elliptic. Apex: Broadly acute. Margin: Entire. Texture: Glabrous, smooth. Color: Upper surface, 186A; lower surface, 185D.

*Peduncles.*—Length: About 1 cm. Angle: Acute at proximal end; toward distal, nodding from weight of flower(s). Strength: Strong, but flexible. Color: 185A.

*Reproductive organs.*—Stamens: Stamen number: Eight. Anther shape: Ovate to cordate. Anther size: About 1 mm. Anther color: 79A. Amount of pollen: Scarce. Pollen color: 79B. Pistils: Pistil number: Four, separate. Pistil length: About 2.8 cm. Style length: About 1.5 cm. Style color: 145B. Stigma shape: Sphere, minute. Stigma color: 145C. Ovary color: 145A.

Disease resistance: Resistance to known Kalanchoe diseases has not been observed to date under commercial practice.

Seed production: Seed production has not been observed.

It is claimed:

1. A new and distinct cultivar of Kalanchoe plant named 'Elves Bells', as illustrated and described.

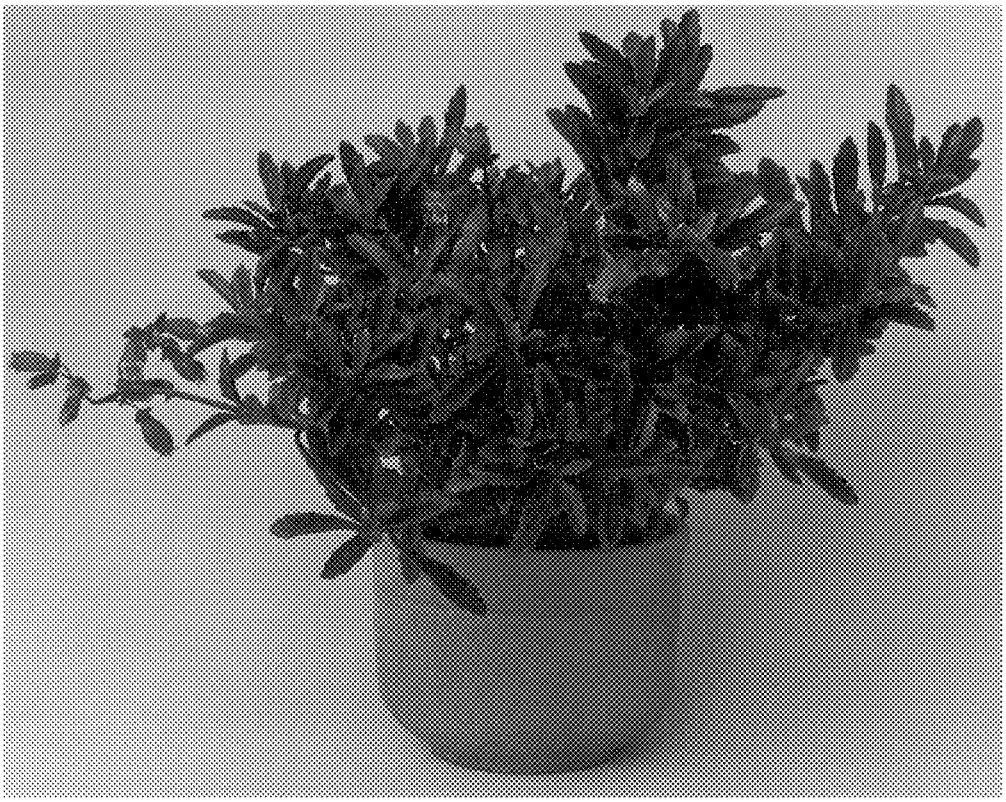
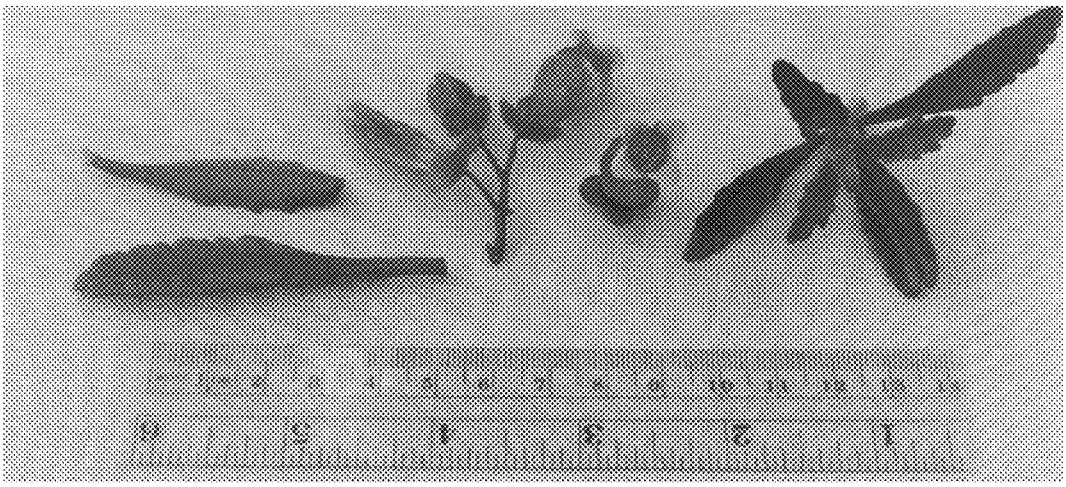

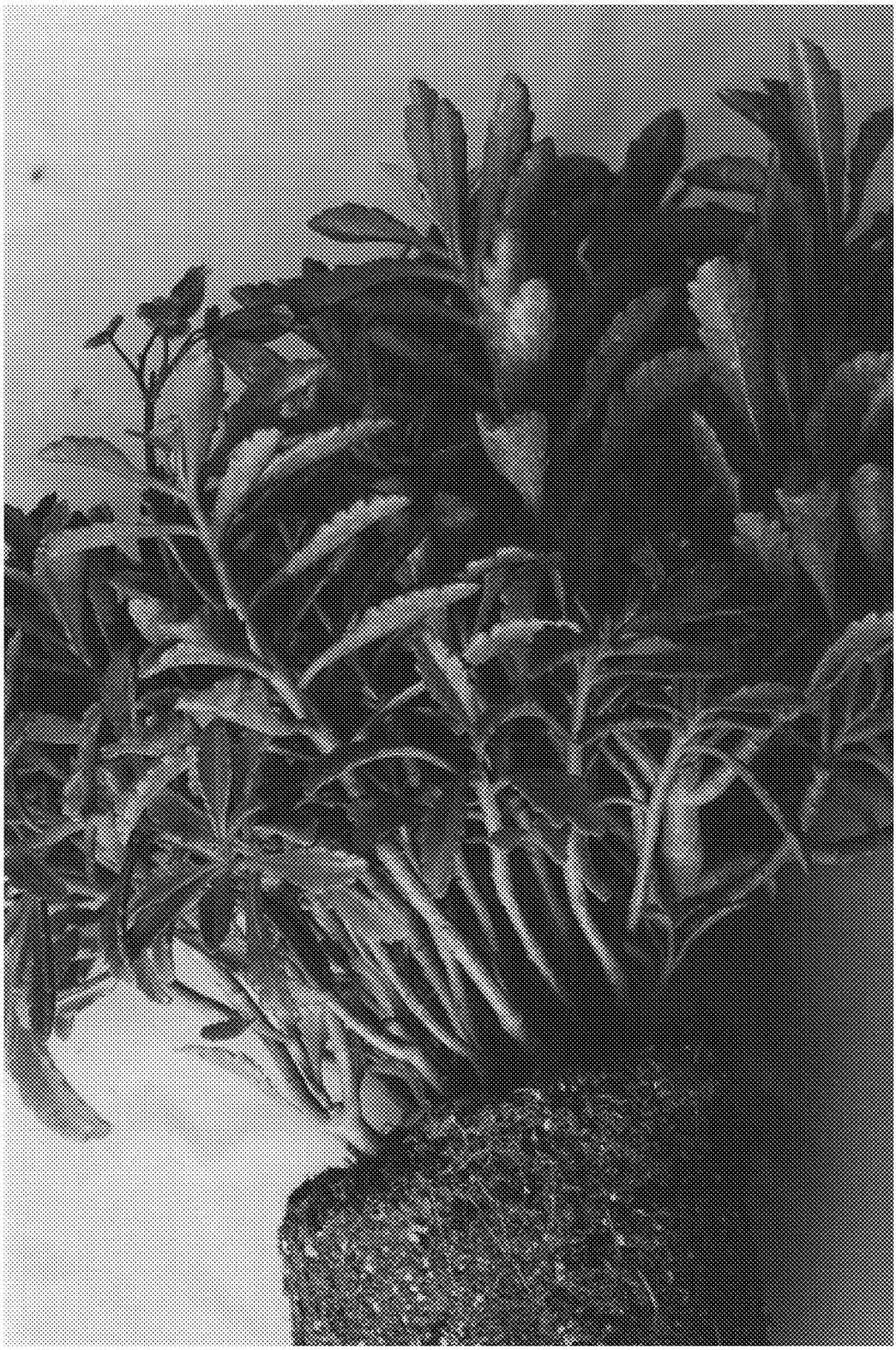

* * * * *